United States Patent [19]
Rosell Ferrer et al.

[11] Patent Number: 6,151,523
[45] Date of Patent: *Nov. 21, 2000

[54] APPARATUS AND PROCEDURE FOR MEASURING VOLUMES AND GLOBAL AND SEGMENTAL CORPORAL COMPOSITION IN HUMAN BEINGS

[75] Inventors: Javier Rosell Ferrer; Pere Riu Costa; Ramón Pallas Areny; Jordi Elvira Cañas; Ramón Bragos Bardia, all of Barcelona, Spain

[73] Assignee: NTE S.A., Barcelona, Spain

[ * ] Notice: This patent issued on a continued prosecution application filed under 37 CFR 1.53(d), and is subject to the twenty year patent term provisions of 35 U.S.C. 154(a)(2).

[21] Appl. No.: 09/034,223

[22] Filed: Mar. 4, 1998

[30] Foreign Application Priority Data

Mar. 6, 1997 [ES] Spain ..................................... 9700499

[51] Int. Cl.[7] ...................................................... A61B 5/05
[52] U.S. Cl. ........................... 600/547; 600/506; 600/507
[58] Field of Search .................................. 600/506, 546, 600/547, 507

[56] References Cited

U.S. PATENT DOCUMENTS 4,911,175  3/1990  Shizgal ..................................... 128/734
5,335,667  8/1994  Cha et al. .
5,579,782  12/1996  Masuo .
5,746,214  5/1998  Brown et al. ........................... 128/693
5,807,272  9/1998  Kun et al. ................................ 600/547

FOREIGN PATENT DOCUMENTS 9300378  2/1993  Spain .

OTHER PUBLICATIONS

The American Journal of Clinical Nutrition article entitled *Estimation of total body water by bioelectrical impedance analysis*[1-3] Robert F. Kushner, MD and Dale A Schoeller, PhD. (1986).

Critical Views in Biomedical Engineering report entitled *Dielectric Properties of Tissues and Biological Materials: A Critical Review* Kenneth R. Foster and Herman P. Schwan (1989).

Primary Examiner—Marvin M. Lateef
Assistant Examiner—Eleni Mantis Mercader
Attorney, Agent, or Firm—Dickinson Wright PLLC

[57] ABSTRACT

Apparatus and procedure for measuring volumes and global and segmental corporal composition in human beings, by means of measuring the electrical impedance at various frequencies, determining in this manner, the ratio between the intracellular water and the extracellular water volumes, the contents of total and extracellular water in each segment and the contents of the segmental lean mass. The apparatus is made up of a computer (11) which controls an electronic box (12), fed through a feeding source (14), various electrodes (13) coming out from said electronic box (12) which are placed on the body under research.

6 Claims, 5 Drawing Sheets

APPARATUS AND PROCEDURE FOR MEASURING VOLUMES AND GLOBAL AND SEGMENTAL CORPORAL COMPOSITION IN HUMAN BEINGS

DESCRIPTION

The present invention refers to an apparatus and a procedure for measuring volumes and global and segmental corporal composition, such as the ratio between intracellular and extracellular water, as well as the ratio between lean mass and fatty mass in human beings.

The measuring equipments currently in existance in the Market, do not offer regional or segmental measurements of the human body, thus enormously limiting the information obtained.

Spanish Patent Application ES 9300378 describes a procedure for the determination of the composition of substances of fleshy nature by means of impedance measurements, but which only uses two measurements determining from them, a value related to the ratio between intracellular water and extracellular water and in consequence, the errors obtained are great. Additionally, said procedure is not capable of extracting any information on the composition of fat in the flesh studied.

A multitude of equations exist which relate the volume content and the corporal composition, all of which introduce errors which may become important and prevent the measurement of significant changes in the body, both in volume and in composition, if used with a very reduced number of experimental data, as happens in the procedure described in document ES 9300378.

Consequently, the object of the present invention is to provide a procedure and a measuring apparatus which determine in a more reliable manner, the global and segmental corporal composition, especially the ratios between the volumes of intracellular water and extracellular water, as well as the ratio between fatty mass and lean mass of the body under research.

This task is solved by means of the procedure and the apparatus of the present invention, which permits the measurement of the volume and the corporal composition, both globally and segmentally, by means of a series of measurements of the electrical impedance at various frequencies, at least four, in the range of 1 kHz to 1 MHz. With the values obtained, first a parameter K is calculated, given by the quotient between the impedance module Z(BF) at a low frequency, between 1 kHz and 50 kHz, and the impedance module Z(AF) at a frequency between 100 kHz and 1 MHz, which serves as an estimation of the ratio between the volumes of intracellular water and extracellular water. This value is independent from the contour conditions of the measurement. The experimental values are herewith adjusted, both at global level and at segmental level with the function:

$$Z(f) = R_\infty + \frac{R_0 - R_\infty}{1 - \left(j\frac{f}{f_c}\right)^{1-\alpha}}$$

by means of the least squares from which the adjustment parameters $R_\infty$, $R_0$, $f_c$ and $\alpha$ are determined, which represent the resistance at infinite frequency, the resistance at zero frequency, the frequency at which the maximum of Im(Z) occurs and the dispersion of the cells size of the biological system, respectively. Parting from these adjustment parameters the following values are calculated:

a) E, defined by:

$$E(\%) = \frac{R_0 - R_\infty}{R_\infty}$$

which reflects the ratio between the volumes of intracellular water and extracelllar water;

b) the total water content of a segment i($TBW_{seg,i}$), given by:

$$TBW_{seg,i} = ko_{TBW\ seg,i} + \frac{K_{TBW} \cdot H^2 \cdot L^2_{seg,i}}{\text{Real }[Z(\infty)]}$$

and the content of a segment i in extracellular water ($ECW_{seg,i}$) which is determined by:

$$ECW_{seg,i} = ko_{ECW_{seg,i}} + \frac{K_{ECW} \cdot H^2 \cdot L'^2_{seg,i}}{\text{real }[Z(10\text{ KHz})]}$$

h being the height of the body in cm, $K_{TBW}$ a proportionality constant for the total water (TBW) and $K_{ECW}$ proportionality constant for the extracellular water, $ko_{TBW_{seg,i}}$ the independent term of segment i, $ko_{ECW_{seg,i}}$ is for extracellular water (ECW) for segment i, $L_{seg,i}$ and $L_{seg,i}'$ geometric terms to be determined for each segment; corresponding the real value [Z($\infty$)] at the real value of an impedance over 100 kHz and less at 1 MHz for segment i, but preferably at R$\infty$, and the real value [Z(10 kHz)] at the real value of an impedance over 10 kHz and below 50 kHz for segment i, but preferably at $R_0$;

The obtention of the coefficients is conducted as follows:

1. having a stadistically significant sample of subjects, the volumes of the total and the global and segmental extracellular water are measured by means of different methods to those presented in this patent.
2. adjusting by lineal regression of least squares between the total and extracellular global volumes and the ratios:

$$\frac{H^2}{\text{Re }[Z(0)]} \text{ and } \frac{H^2}{\text{Re }[Z(\infty)]}$$

respectively, (where Z is the right side impedance, that is to say, that of the right arm and leg plus that of the trunk measure in series at one time) slopes $K_{ECW}$ and $K_{TBW}$ are respectively obtained.

3. adjusting by lineal regression of the least squares among the ratio:

$$\frac{H^2 \cdot K_{TBW}}{\text{Re }[Z(\infty)]}$$

(where Z is segmental) and the segmental total water measured, a slope $L^2_{seg,i}$ is obtained for each i segment, and an independent term $ko_{TBW,seg\ i}$ for each segment.

4. adjusting by lineal regression of least squares between the ratio:

$$\frac{L^{2seg,i} \cdot H^2 \cdot K_{ECW}}{Re\,[Z(0)]}$$

(where Z is segmental) and the segmental extracellular water measured with another method, a slope $\psi_i$ is obtained for each segment i and an independent term $ko_{ECW,seg\,i}$ for each segment i.

5. next an extracellular water formula $L^2_{seg,I}$ is replaced by $$L'^2_{seg,i} = \phi i \cdot L^2_{seg,i};$$

$L'_{seg,i}$ and $L_{seg,i}$ include geometric information within the determination formulas of volumes.

c) the contents of segment i in intracellular water which is determined by means of the subtraction of $ECW_{seg,i}$ from $TBW_{seg,i}$ d) of the total and extracellular water at global level which is determined by the sum of the respective values of segments i e) the segmental or regional lean mass content $MM_{seg,1}$ and the global by means of equation.

$$MM_{seg,i} = Lean\,Mass = N + M \cdot \frac{D^2_{eq}seg.i}{R(AF)}$$

N and M being terms which are introduced form the lineal regression between relation $$\frac{D^2_{eq}, seg, i}{Re\,[Z(\infty)]}$$

and the average lean mass value by means of an alternative method and which shall depend on the type of human race, and $D^2_{eq.seg,i}$, a geometric parameter of segment i, obtaining the global value of the amount of lean mass and the sum of all the $MM_{seg,i}$ values and the global fatty mass of the difference between the weight of the human body studied and the weight of the amount of global lean matter.

Additionally the task of this invention is solved because the previously described procedure is conducted by means of a measuring apparatus which consists of a rear connection board (backplane) which interconnects four boards and an electric source, said boards consisting of a signal generator board which generates two or more selectionable frequencies as well as reference signals for the demodulation, in an interface board with the user who converts the tension signals generated into current, into a board for signal detection (signal detection board) which is made up of a differential amplifier and a gain amplifier with selectionable gain by means of software, into an A/D obtention board which is provided with a A/D converter of preferably 16 bits for sampling for data obtention.

The electrical source is connected to the body under study by means of a multiplexor which permits any electrode couple to be connected to the said source, connecting each one of the electrodes to an in-put buffer whilst each one of their out-puts is connected to a multiplexor circuit. This multiplexor feeds a differential amplifier, by means of shielded coaxial cables. The control of the system is conducted by means of a microcontroller.

The procedure and the apparatus of the present invention is herewith described by means of an embodiment example, with the help of the drawings in which.

The apparatus and the procedure, which are the object of the invention, are based on the study of a physical phenomenon which is denominated relaxation in the electrical impedance signal. This phenomenon is explained in total detail by K. Forster and H. Schwan, "Dielectric Properties of Tissues and Biological Materials: A Crucial Review" in Critical Reviews in Biomedical Engineering, volume 17, part 1 (1989). This relaxation consist of a fall in the electrical impedance value with the electrical signal frequency used to measure the same in any medium whatsoever. The electrical impedance of a medium is broken up into a real part and another imaginary part. The real part is what is commonly known as electric resistance and the imaginary part, in the case of biological tissues, corresponds to the electric capacity of the medium in question. The relaxation phenomenon has its explanation in the absorption of electromagnetic energy. A simple electric model is accepted by conviction where the capacitance character of the cellular membrane produces said absorption of energy (FIG. 2). The resistance of the extracellular medium is modelled by a $R_e$ resistance and the intracellular medium resistance is modelled by another $R_i$ resistance. The capacity of the cellular membrane is modelled by a C capacitor. When the Z electric impedance is measured based on the f frequency in a circuit such as the one presented in FIG. 2, a graph is obtained such as the one presented in FIG. 1. If the injected signal is of high frequency, an electric impedance is obtained which is equal to the parallel of the two resistances of the circuit and if it is of low frequency, it is equal to the extracellular Re resistance.

The frequency at which the fall of the impedance is presented depends on the type of cell as an average of the measured biological system. The animal cells, for example, have a relaxation frequency below that of bacteria. In consequence, the measurement of the electric impedance at various frequencies by the apparatus of the present invention permits a determination of the type of average cell existing in the human body or region of the latter which is being measured.

Figure 3:
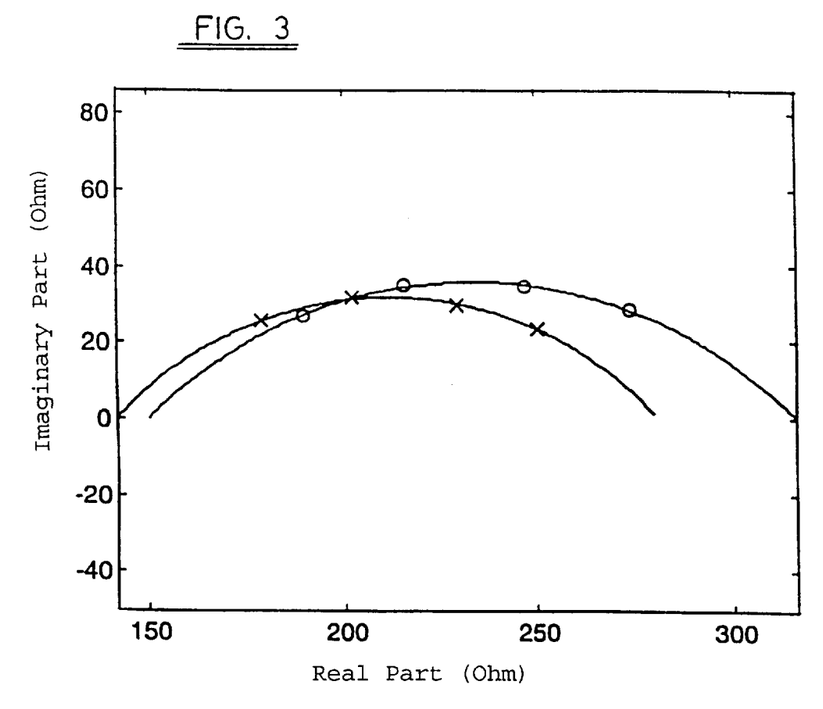
FIG. 3 shows two spectra of the complex impedance based on the frequency.

FIG. 3 presents a form of representing the impedance of a biological system (a curve corresponds to a segment and the other to the impedance of the right hand side), that is to say, the imaginary part of the impedance based on the real part. In said drawing, the impedance of a biological system can be seen to draw a flat half-circumference. This graph is well known and is denominated Cole-cole graph. The cut frequency may be seen as the point where the complex part of the impedance presents the highest value. The flattening of the half-circumference is related to a parameter called $\alpha$. Other two parameters are $R_0$ and $R\infty$ and obtains the value of the real part of the impedance in direct current and at very high frequency (over 1 MHz) by means of the extrapolation of the adjustment without requiring to measure it. That is to say, four parameters are available which describe the human body or region of the latter which is measured: resistance in direct current $R_0$, resistance at very high frequency $R\infty$, cut frequency $F_c$ and flattening value of the half-circumference $\alpha$.

In the procedure of the present invention, the composition of the researched body is obtained, parting from said 4 parameters.

Figure 1:
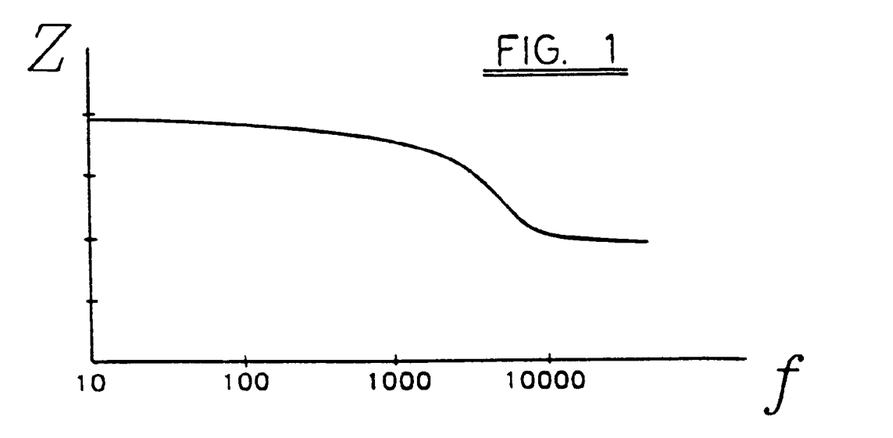
FIG. 1 shows a spectrum of the electrical impedance module based on frequency f.
Figure 2:
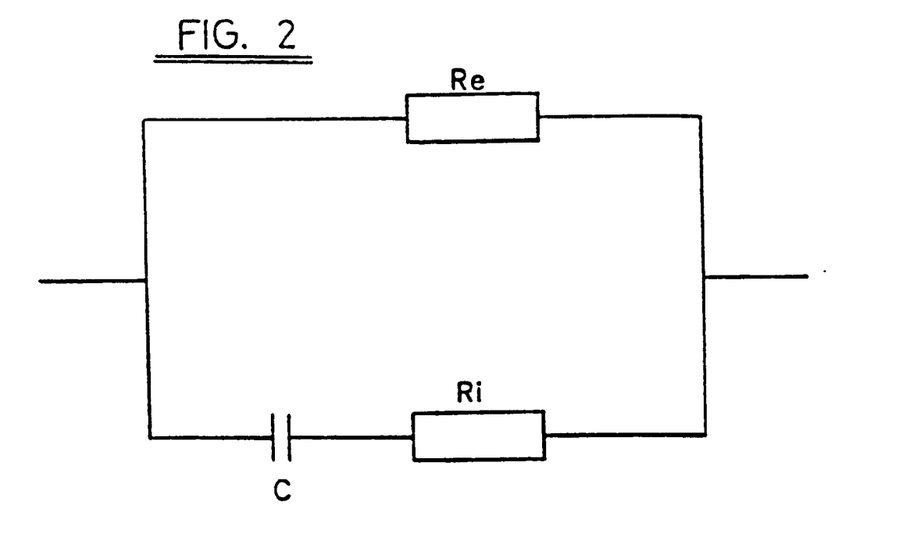
FIG. 2 shows a schematic diagram of connections corresponding to the electrical constelation of a body.

1) Measurement of the electrical impedance with a frequency scan of 1 kHz at 10 MHz to obtain the graph of FIG. 1. Four measuring points in the said range is the minimum number of measurements required for reproducing the curves of FIGS. 1 and 3. The measurement is conducted by injecting an electric current of determined frequency through two electrodes connected to the skin and measuring the fall of the current tension applied through the other two electrodes, also connected to the skin. This is the base of the impedance measurement at four wires which is very resistant to the influence of the electrode impedance. This measurement of impedance is conducted with currents of various frequencies until a minimum of 4 points of frequency are obtained in the range of 1 kHz to 1 MHz and this is repeated for each segment i.

2) On the body, 11 electrodes may be placed with the apparatus which is the object of the invention. Grouping said electrodes in 4's, up to 7 segments or human regions are obtained. The distribution of regions which are given in default in the measuring apparatus is the result of placing the 11 electrodes according to FIG. 7. This placement of electrodes permits the measurement of the impedance at various frequencies according to the process of point 1 for the following segments: head and neck, right arm, left arm, thorax, abdomen, right leg and left leg. Other distributions of regions is possible and it only requires the distribution in 4's of the 11 electrodes until 7 segments are made. The measuring apparatus permits the selection of injecting electrodes and tensiometers. This permits any type of electrode to be injector or measurer.

3) Obtention of an assembly of experimental data on electrical impedance at frequencies of 1 kHz to 1 MHz, regional and global of the human body.

Parting from this point, the procedure, according to the present invention, processes this assembly of data in different ways to obtain a set of information which will permit to know the volumes and corporal composition of the human body measured.

The first stage of the procedure is the obtention of parameter K. It is a first simple calculation to be conducted by the meeasurer to permit the ratio between the total water and the extracellular water volumes in the body being studied and is conducted as follows:

1) K is obtained by the quotient of an impedance value at low frequency (between 1 kHz and 50 kHz) and one at high frequency (over 100 kHz up to 1 MHz):

$$K = \frac{|Z(BF)|}{|Z(AF)|}$$

where $|Z(AF)|$ and $|Z(BF)|$ are the values of the module of the electrical impedance at high and low frequency respectively 2) This ratio is associated to the ratio of volumes of the extracellular water of the total water of the body. This ratio is conducted both at global and at segmental level.

The second stage corresponds to a more complete study of the obtained data. This study consists of the adjustment of the Cole-cole model to the data by means of the following steps:

1) The electrical impedance measurements resulting from the scanning in frequency (at least four measurements of 1 kHz to 1 MHz) and at global and segmental level are adjusted by the function:

$$Z(f) = R\infty + \frac{R_0 - R\infty}{1 + \left(j\frac{f}{f_c}\right)^{1-\alpha}}$$

by means of an adjustment of least squares. This function simulates the dependence of the electrical impedance (Z) as regards frequency f. The adjustment parameters $R_0$ and $R\infty$ are the resistances which present the medium in direct current and at very high frequency respectively, $f_c$ is the frequency at which the maximum of the imaginary part is produced and depends on the type of cell measured in the biological system; and a is a parameter which is related to the dispersion of dimensions of the cells of the measured biological system. The expression of this point 1 reproduces the curve of FIG. 3 which would be obtained if a great amount of points were measured.

2) Parting from the first two adjustment parameters found ($R_0$ and $R\infty$) we obtain a value called E which gives the relation between the intracellular water and the extracellular water volumes:

$$E(\%) = \frac{R_0 - R\infty}{R\infty}$$

The impedance measured may be modelled as the previously described circuit which is presented in FIG. 2. The ratios between the parameters of circuit ($R_e$ and $R_i$) with that of the mathematical model are as follows:

$$R_e = R_0$$

$$R_i = \frac{R_0 \cdot R\infty}{R_0 - R\infty}$$

3) The series of parameters obtained from the adjustment are associated to characteristics of composition of the body at global and segmental level:
  a) Ratios of E, which give an idea of the ratio between volumes of extracellular and intracellular water.
  b) Cut frequency ($f_c$), and
  c) flattening of the curve presented in FIG. 3 ($\alpha$).

The third stage will offer information on the corporal volumes and will permit the studying of its changes. This procedure uses the impedance at 10 Khz and at a greater frequency than 100 kHz or else parameters $R_0$ and $R\infty$ obtained by the previous stage. The steps to be followed are 1) The necessary values are parameters $R_0$ and $R\infty$. These parameters are introduced in the following formulas to determine the volume of total water and extracellular water:

$$TBW_{seg,i} = ko_{TBWseg,i} + \frac{K_{TBW} \cdot H^2 \cdot L^2_{seg,i}}{real[Z(\infty)]}$$

$$ECW_{seg,i} = ko_{ECWSeg,i} + \frac{K_{ECW} \cdot H^2 \cdot L^2_{seg,i}}{\text{real}[Z(10 \text{ kHz})]}$$

where $TBW_{seg,i}$ is the content of segment i in total water and $ECW_{seg,i}$ the content of segment i in extracellular water, H is the height of the body in cm, $K_{TBW}$ is proportionality constant for the total water (TBW) and $K_{ECW}$ for the extracellular water, $ko_{TBWseg,i}$ is the independent term for the total water equation (TBW) of segment i, and $ko_{ECWseg,i}$ for the extracellular water (ECW) of segment i. $L_{seg,i}$ and $L'_{seg,i}$ are geometric terms to be determined for each segment i. The obtention of the coefficients is conducted in the following manner:

a) with a stadistically significant sample of subjects, the volumes of total and global and segmental extracellular water are measured by means of methods other than those which are presented in this patent.

b) Adjusting by lineal regression of least squares between the total and extracellular global volumes and the ratios:

$$\frac{H^2}{\text{Re}[Z(0)]} \text{ and } \frac{H^2}{\text{Re}[Z(\infty)]}$$

respectively, where Z is the right hand side impedance, that is to say, that of the right arm and leg plus that of the trunk, the slopes $K_{ECW}$ and $K_{TBW}$ are respectively obtained.

c) adjusting by lineal regression of the least squares between the ratios;

$$\frac{H^2 \cdot K_{TBW}}{\text{Re}[R(\infty)]}$$

(where Z is segmental) and the segmental total water measured, a slope $L^2_{seg,i}$ is obtained for each segment i and an independent term $ko_{TBW,seg\ i}$ for each segmenti d) adjusting by lineal regression of the least squares between the ratios:

$$\frac{L^2_{seg,i} \cdot H^2 \cdot k_{ECW}}{\text{Re}[Z(0)]}$$

(where Z is segmental) and the segmental extracellular water measured by means of another method, a slope $\psi_i$ obtained for each segment i and an independent term $ko_{ECW,seg\ i}$ for each segment i.

e) a change is conducted on formula $L^2_{seg,i}$ of extracellular water by $$L'^2_{seg,i} = \phi_i L^2_{seg,i};$$

$L'^2_{seg,i}$ and $L_{seg,i}$ include geometric information within the formulas for volume determination.

These equations provide the value of the total water and of the extracellular water for segment i. The real value $[Z(\infty)]$ corresponds to $R_\infty$ or to the real value of an impedance over 100 kHz and below 1 MHz for segment i; and the real value $[Z(10\text{ kHz})]$ corresponds to $R_0$ or to the real value of a superior impedance at 10 kHZ and below 50 kHz for segment i.

Parameters $K_{TBW}$, $K_{ECW}$, $ko_{seg,i}$, $ko_{seg,i}$, depend on the race the human body belongs to and are adjusted by means of calibration. Values $ko_{seg,i}$, $ko_{seg,\ i}$ additionally depend on the segment in question. Values $L_{eq}$ and $L'_{eq}$ provide geometric information of the segment in question.

2) The values of the total water and of the extracellular water are obtained according to the given formulas. The segments in question may be, for example; head and neck, thorax, abdomen, legs and arms, and are obtained with the distribution of electrodes (0 to 10) of FIG. 7. For other segments, new values of $ko_{seg,i}$, $ko_{seg,i}$ and $L_{eq}$ shall be adjusted. The values of the intracellular water volume is obtained from the subtraction of the volume of extracellular water of the total water volume.

3) The value of the volume of total and extracellular water for all the body, that is to say, at global level, is calculated as the sum of all the segments i mentioned in point 4 (for example, head and neck, right leg, left leg, thorax, abdomen, right arm and left arm). The global values may also be obtained using the RSI (Right Side Impedance (impedance of the right side) which is constituted by the right leg and arm plus trunk, as if it were a segment, conveniently considering the specific parameters of the formula for this segment. Said impedance of the right side is extensively described in: Kushner R. F., and Schoeller D. A., "Estimation of Total Body Water by Bioelectrical Impedance Analysis", Am. J.Clin. Nutr. 44, 417–424 (1986). The global value of the intracellular water volume is obtained by the substraction of the extracellular water volume from the total water volume.

The global values of the water volume calculated according to the third stage produce according to the same, much more exact values than those using the RSI according to the formulas in compliance with the state of the art.

The fourth stage to be conducted provides information on the content of the lean mass both segmental and global. Said stage follows the next steps:

1) Using the resistance value at high frequency (equal or over 100 kHz) for the obtention of the amount of fat which is presented according to the following expression:

$$MM_{seg,i} = \text{Lean Mass} = N + M \cdot \frac{D^2_{eg,seg,i}}{\text{Re}[Z(0)]}$$

N and M being terms which are introudced from the lineal regression between the ratio.

$$\frac{L^2_{eq,seg,i}}{\text{Re}[Z(\infty)]}$$

and the value of lean mass measured by means of an alternative method and which depends on the type of human race, and $D^2_{eq,seg,i}$, a geometric parameter of segment i, obtaining the global value of the amount of lean mass from the sum of all the $MM_{seg,i}$ and the amount of global fatty mass of the difference between the weight of the human body studied and the weight of the amount of global lean matter.

2) The value of the amount of global lean matter of the body shall be obtained from the sum of all the amount of segmental or regional lean matter.

3) The value of the amount of global fat shall be obtained by substracting from the weight of the human body studied, the amount of global lean matter obtained by the sum of all the amount of segmental lean matter.

All the stages may also be used for measuring the quantity of segmental lean matter from any region which is defined outside those previously indicated (head and neck, right leg, left leg, right arm, left arm, thorax and abdomen). Using only two pairs of electrodes from the system, any anatomical region of measurement may be defined.

These four stages use the electrical impedance values, both real part and imaginary part, measured within a frequency range between 1 kHz and 1 MHz.

Figure 4:
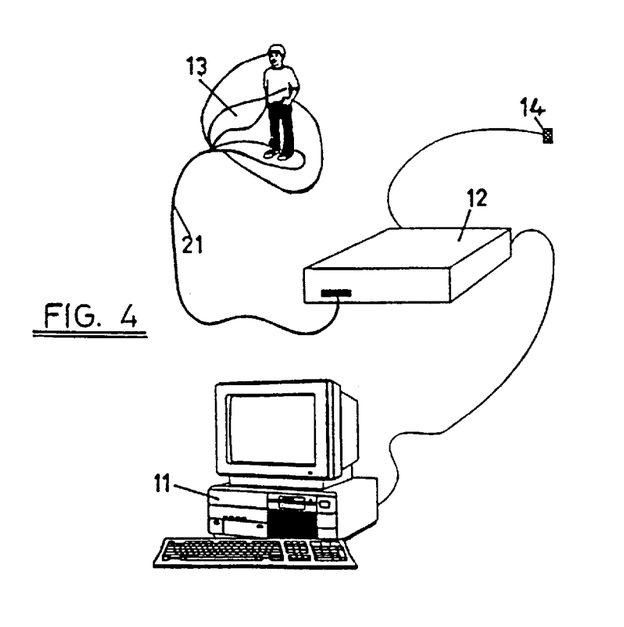
FIG. 4 shows an embodiment example of the measuring apparatus according to the invention.
Figure 7:
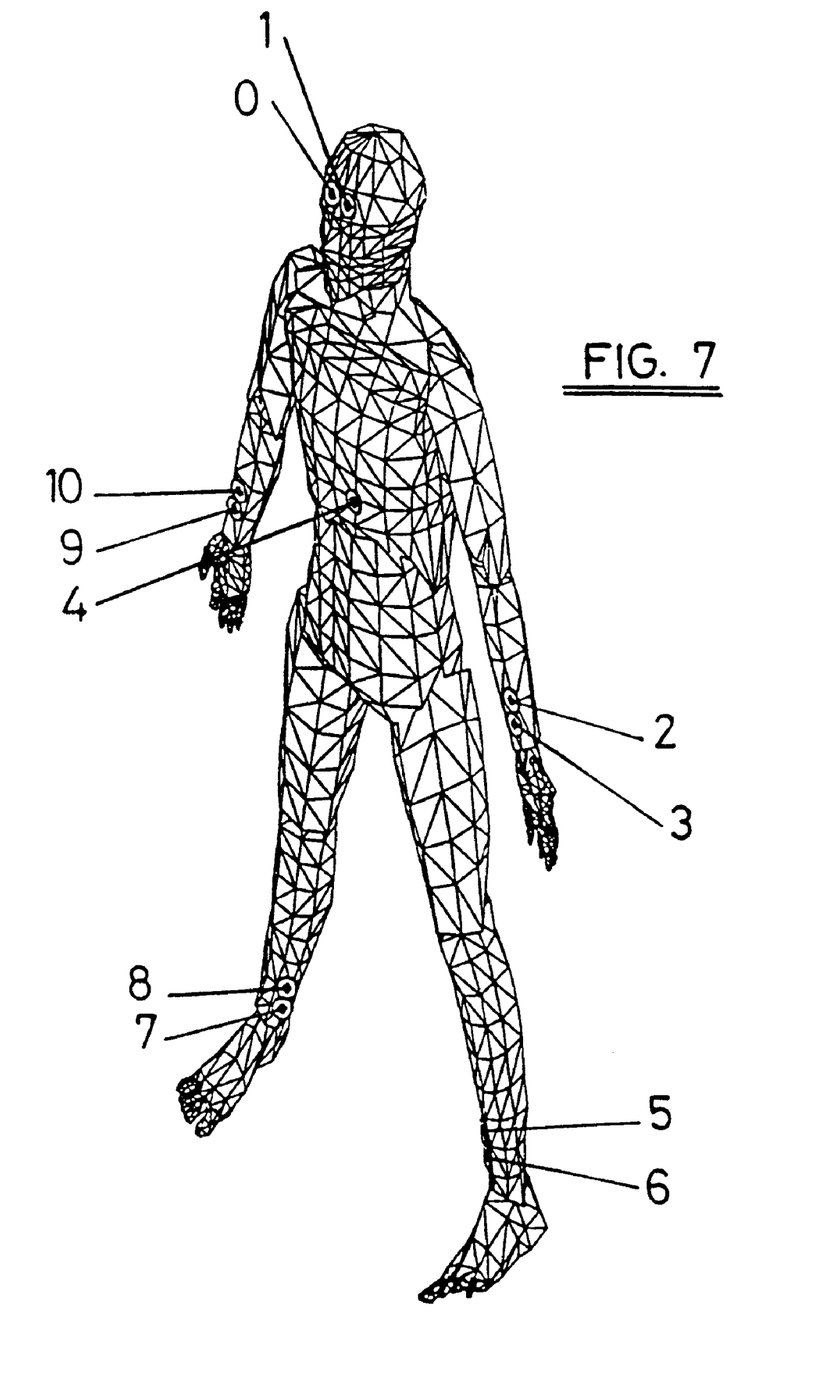
FIG. 7 shows the zones of the body in which the electrodes are placed.

The apparatus which is also th object of this invention, is a measuring apparatus of electrical impedance at various frequencies. This impedance measuring aparatus measures both the real part and the imaginary part at eight frequencies selected by the user. These eight frequencies may go from 1 kHz to 1 MHz. The measuring apparatus is made up of a computer (11) which controls an electronic box (12), fed through the feeding source (14) coming out from said electronic box (12), in a preferred manner, eleven electrodes (13) which are placed, for example, as shown in FIG. 7. FIG. 4 presents the concept of the system.

As may be observed in FIG. 7, four electrodes (2, 3, 9, 10) are placed at the ends of the forearm, four at the ends of the legs (5, 6, 7, 8), two (0,1) on the forehead and one (4) on the point of the breastbone. These electrodes are used as injectors and/or detectors for measuring all the segments which make up the body and which have been previously indicated. Other combinations of electrodes may be chosen to create other regions which shall not necessarily be such, that will give, after summing them up, the totality of the human body.

Figure 5:
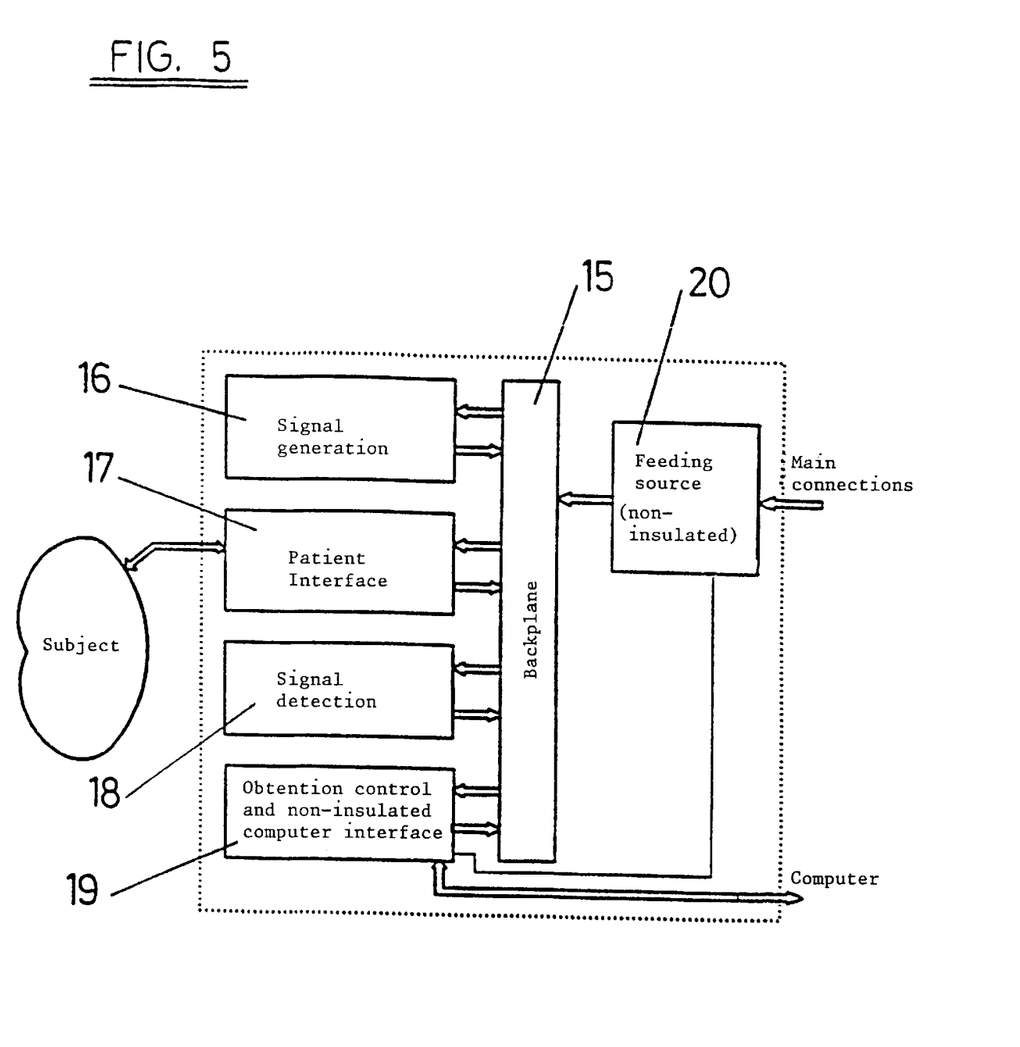
FIG. 5 shows the block diagram of the apparatus of FIG. 4.

The measuring apparatus which is the object of the present invention, is designed according to a block diagram such as the one presented in FIG. 5. The apparatus is formed by a rear connection board, (backplane) (15) which interconnects four boards (16, 17, 18, 19) and an electric source (20). The board (16) of the generator for the signal (signal generator) generates two selected frequencies and reference signals for demodulation. The board (17) for interface with the user (patient interface) converts the generated tension signals into current, the board (18) for detection of the signal is made up of a differential amplifier and gain amplifier with selected gains via software. Then, the signal is demodulated, using four analogical multipliers and four integrators, the board (19) for A/D obtention is provided with an A/D convertor of preferably 16 bits for sampling, for the obtention of data. The control of the system is conducted by a microcontroller. The microcontroller sends orders to the other boards of the system.

The electrical source (20) is connected to the body under study through a multiplexor which permits any pair of electrodes to connect to the said source. Each one of the eleven electrodes (0 to 10) are connected to an in-put buffer using shielded coaxial cables (21). Each out-put of the buffer is connected to a multiplexor circuit which feeds a differential amplifier. Five buffers are available plus those to which internal calibration impedances are connected.

Figure 6:
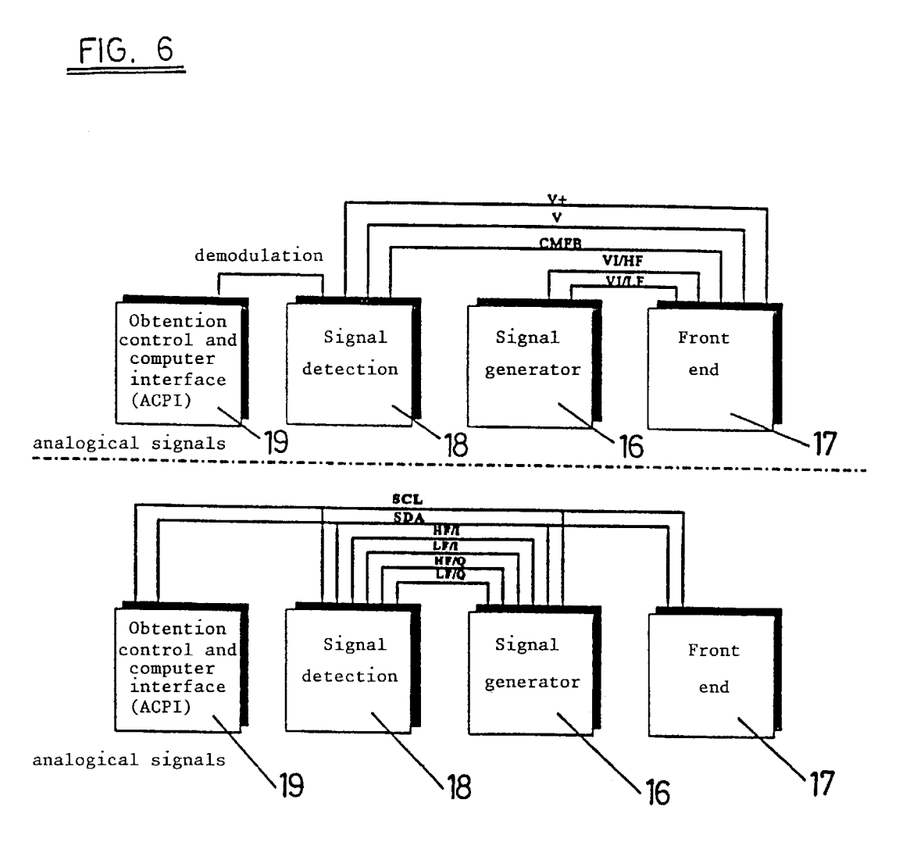
FIG. 6 shows the interconnections between the diverse boards.

The interconnections between the board (19) for A/D obtention, the board (18) for signal detection, the board (16) of the signal generator and the front end (17) are presented in FIG. 6.

With this measurer and the procedure previously presented, a highly reliable tool is available for the measurement of the amount of fluids and corporal composition.

Adding an accelerometer to this measurer which is the object of the invention, another additional application may be conducted for the use of the electrical impedance to various frequencies for the follow-up of fluid displacement in the human body. Such an accelerometer may be included as an element of the patient interface 17. This application consists of the follow-up of corporal fluid displacements in a human being when subjected to different accelerations other than those accelerations produced by the terrestial gravitational fields. In consequence, the following measuring apparatus is proposed as additional object of the invention. This systemm consists of an apparatus such as the one previously presented with an incorporated accelerometer. The electrical impedance and the acceleration measurements are synchronized. The electrodes may be reduced in this case to those which offer the following segments: head and neck, right or left leg, right or left arm, thorax and abdomen. The electrodes are reduced in the latter case to 7 which is according to the numbering of FIG. 7: (0, 1, 4, 2) and (3) (or 9 and 10), (5) and (6) (or 7 and 8). The reduction of electrodes may be assumed considering that the changes shall be symetrical in the human body under study.

This latter apparatus, fruit of the extension of the first presented, is a tool of great utility for the follow-up of the movement of fluids between the corporal regions during centrifuge pilot training and during military flights, for the control of anti-g suits.

What is claimed is:

1. A method for measuring volumes and global and segmental corporal composition in human beings comprising:

measuring the electrical impedance at a plurality of locations corresponding to a plurality of predeteremined segments of a human body, using a minimum of four frequencies in the range of 1 kHz to 1 MHz, estimating the ratio between the total water and extracellular water volumes, both at global and segmental levels, by determining the k quotient between the impedance module at low frequency Z(BF), placed between 1 kHz and 50 kHz, and the impedance module at high frequency Z(AF), placed between 100 kHz to 10 MHz, said quotient being independent from the conditions of the measurement contour, adjusting said quotient by the least squares method, both at global and segmental levels, by the following electrical impedance expression (Z) based on the frequency (f);

$$Z(f) = R_\infty + \frac{R_0 - R_\infty}{1 - \left(j\frac{f}{f_c}\right)^{1-\alpha}}$$

thus determining the values $R_\infty$, $R_0$, $f_c$ and $\alpha$, wherein $R_{28}$ represents the resistance at infinite frequency, $R_0$ represents the resistance at zero frequency, $f_c$ represents the frequency at which the maximum of lm(Z) occurs and $\alpha$ represents the dispersion of the cells of the biological system, with which the following values are calculated:

a) the ratio between the intracellular water and extracellular water volumes, given by;

$$E = \frac{R_0 - R\infty}{R\infty}$$

b) the total water content of a segment i ($TBW_{seg,i}$), given by:

$$TBW_{seg,i} = ko_{TBW\ seg,i} + \frac{K_{TBW} \cdot H^2 \cdot L_{seg,i}^2}{\text{Real}[Z(\infty)]}$$

and the content of a segment i in extracellular water ($ECW_{seg,i}$) which is determined by:

$$ECW_{seg,i} = ko_{ECW_{seg,i}} + \frac{K_{ECW} \cdot H^2 \cdot L_{seg,i}'^2}{\text{real}[Z(10\ \text{KHz})]}$$

wherein H is the height of the body in cm, $K_{TBW}$ is a constant of proportionality for the total water (TBW), $K_{ECW}$ is a constant of proportionality for the extracellular water, $Ko_{TBWseg,i}$ is the independent term for segment i, $Ko_{ECWseg,i}$, is the independent term for the extracellular water (ECW) for segment i, and $L'_{seg,i}$ and $L'_{seg,i}$ are geometric terms to be determined for each segment I, wherein the real value ($Z(\infty)$) corresponds to the real value of an impedance over 100 kHz and below 1 MHz for segment i, but preferably at R∞, and the real value ($Z(10\ kHz)$) corresponds to the real value of an impedance over 10 kHz and below 50 kHz for segment i, but preferably at $R_0$;

c) the content of segment i in the intracellular water which is determined by means of the subtraction of $ECW_{seg,i}$ from $TBW_{seg,i}$;

d) the volume of total and extracellular water at the global level which shall be determined by the sum of the respective values of segments i;

e) the content of the segmental or regional $MM_{seg,i}$ and global lean mass by means of the equation $$MM_{seg,i} = \text{Lean Mass} = N + M \cdot \frac{D^2_{eq,seg,i}}{R(AF)}$$

N and M being terms which are introduced from the lineal regression between the ratio:

$$\frac{D^2_{seg,i}}{Re[Z(\infty)]}$$

and the value of the amount of lean mass measured by means of an alternative method and which depend on the type of human race, and $D^2_{eq,seg,i}$, a geometric parameter of segment i; and     obtaining the global value of the amount of lean mass from the sum of all the values $MM_{seg,i}$ and the global fatty mass from the difference between the weight of the human body studied and the weight of the amount of global lean matter.

2. A method according the claim 1, comprising determining the volume of total and extracellular water at the global level using an RSI (right side impedance) as if it was a segment conveniently considering the specific parameters of the TBW and ECW formulas.

3. An apparatus for measuring the electrical impedance for the method of claim 1 comprising a backplane which interconnects an electrical source and four signal generator boards, wherein a first signal generator board generates at least two of said frequencies as well as reference signals for demodulation, a second board for patient interface converts the tension signals generated into current, a third detection signal board is made up of a differential amplifier and a gain amplifier with selectable gains via software and a fourth A/D obtention board is provided with an A/D converter for sampling for data obtention, wherein said electrical source is adapted to be connected to the human body under study by means of a multiplexor which permits any pair of electrodes to be connected to the said source, by connecting each one of the electrodes to an input buffer, whilst each one of their outputs is connected to a multiplexor circuit which feeds a differential amplifier, and wherein the control of the system is conducted by means of a microcontroller.

4. Apparatus according to claim 3, further comprising an accelerometer which measures acceleration to which the body has been subjected, in a synchronized manner with the impedance measure.

5. A process for measuring the volume and global and segmental corporal compositions in human beings, comprising:

measuring the electrical impedance at a plurality of locations corresponding to a plurality of predetermined segments of a human body, using various frequencies within the range between 1 kHz and 1 MHz;

estimating the ratio between total water and extracellular water volumes, both at global and segmental levels;

adjusting the estimated ratio at both global and segmental levels using the least squares method, wherein preselected parameters can be used to determine the ratio between intracellular and extracellular water volumes, the total water content of one or more predetermined segments, the intracellular water content of said one or more predetermined segments, and the volume of total and extracellular water at the global level, by adding and/or substracting the values associated with said predetermined segments.

6. The process of claim 5, wherein said parameters are used to determine the ratio, at both global and segmental levels, of lean mass to fatty mass within said human being.

* * * * *